United States Patent [19]

Buzby, Jr.

[11] Patent Number: 4,720,580
[45] Date of Patent: Jan. 19, 1988

[54] N-(AMINOALKYLENE)BENZENESULFONA-MIDES

[75] Inventor: George C. Buzby, Jr., Blue Bell, Pa.

[73] Assignee: American Home Products Corporation, New York, N.Y.

[21] Appl. No.: 850,805

[22] Filed: Apr. 11, 1986

Related U.S. Application Data

[63] Continuation-in-part of Ser. No. 653,757, Sep. 21, 1984, abandoned.

[51] Int. Cl.[4] .............................................. C07C 143/78
[52] U.S. Cl. .......................................... 564/89; 564/90
[58] Field of Search ..................... 564/89, 90; 514/604

[56] References Cited

U.S. PATENT DOCUMENTS 2,233,296   2/1941   Nelles et al. ........................... 564/94

FOREIGN PATENT DOCUMENTS 1912851   3/1968   Fed. Rep. of Germany .

OTHER PUBLICATIONS

Derwent: 64655R, Abstract of U.S. Pat. No. 3,527,801.
Derwent: 24510F, Abstract of U.K. No. 1053204.
Derwent: 10090F, Abstract of Japanese 26169/63.
Derwent: 84–115871/19, Abstract of EP 107350.

Shoeb et al., Ind. J. of Chem. 3(11)507–9 (1965).
Dauksas et al., "Chem. Abst." vol. 61, (1964), 13304f&g.

Primary Examiner—Anton H. Sutto
Attorney, Agent, or Firm—Richard K. Jackson

[57] ABSTRACT

This invention provides a group of anti-arrhythmic agents of the formula:

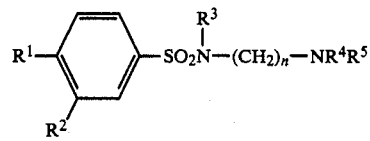

in which
  $R^1$ is hydrogen, hydroxy, alkoxy or halo;
  $R^2$ is hydrogen, alkoxy, halo or trifluoromethyl, with the proviso that $R^2$ is not hydrogen when $R^1$ is hydrogen;
  $R^3$ is alkyl or, when $R^2$ is trifluoromethyl and $R^1$ is hydrogen, $R^3$ may be hydrogen;
  $R^4$ is alkyl, cycloalkyl or cycloalkylmethyl;
  $R^5$ is hydrogen or alkyl;
  n is 2–4;
or a pharmaceutically acceptable salt thereof.

14 Claims, No Drawings

N-(AMINOALKYLENE)BENZENESULFONAMIDES

This application is a continuation-in-part of co-pending U.S. patent application Ser. No. 653,757, filed Sept. 21, 1984, abandoned.

DESCRIPTION OF THE INVENTION

In accordance with this invention, there is provided a group of antiarrhythmic agents of the formula:

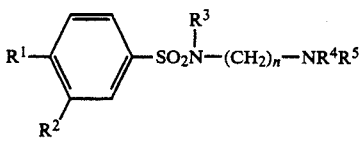

in which
$R^1$ is hydrogen, hydroxy, alkoxy of 1 to 6 carbon atoms or halo;
$R^2$ is hydrogen, alkoxy of 1 to 6 carbon atoms, halo or trifluoromethyl, with the proviso that $R^2$ is not hydrogen when $R^1$ is hydrogen;
$R^3$ is alkyl of 1 to 6 carbon atoms or, when $R^2$ is trifluoromethyl and $R^1$ is hydrogen, $R^3$ may be hydrogen;
$R^4$ is alkyl of 1 to 6 carbon atoms or cycloalkyl of 5 to 7 carbon atoms or cycloalkylmethyl of 6 to 8 carbon atoms;
$R^5$ is hydrogen or alkyl of 1 to 6 carbon atoms; and, n is one of the integers 2, 3 or 4;
or a pharmaceutically acceptable salt thereof.

Among the compounds of the above-described genus there resides a preferred group of compounds from the standpoint of production economics and activity profile which may be described by the formula:

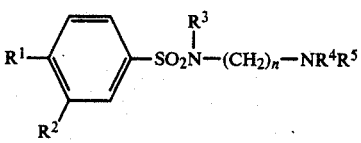

in which
$R^1$ and $R^2$ are alkoxy of 1 to 6 carbon atoms or halo or $R^1$ is hydrogen and $R^2$ is trifluoromethyl;
$R^3$ is alkyl of 1 to 3 carbon atoms or, when $R^2$ is trifluoromethyl, $R^3$ may be hydrogen;
$R^4$ is alkyl of 1 to 3 carbon atoms;
$R^5$ is hydrogen or alkyl of 1 to 3 carbon atoms; and, n is one of the integers 2, 3 or 4;
or a pharmaceutically acceptable salt thereof.

The pharmaceutically acceptable salts of the antiarrhythmic agents of this invention are prepared directly by neutralization of the free base. These physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The compounds of this invention are prepared by reaction of an appropriately substituted benzene sulfonyl halide with an appropriately substituted α,ω-alkane diamine of 1 to 4 carbon atoms. These reactants are generally known compounds and otherwise are routinely prepared by techniques well within the skill of the chemist.

The compounds of this invention demonstrate antiarrhythmic activity when tested in the standard experimental animal in accordance with the following procedure:

Rats weighing between 400–500 gms were anesthetized with 35–40 mg/kg. Na pentobarbital i.p. Rats were close-clipped on the neck and left side prior to cannulation of the jugular vein and tracheotomy. In some experiments, a catheter was introduced into the carotid artery for measurement of arterial blood pressure. Respiration was provided by a Harvard Model 681 respirator at a rate of approximately 55/min and a volume of 4 cc per cycle. The rat was then placed upon its right side and the heart was exposed by making an incision and separating the ribs. 4-0 silk on taper RB-1 needle was passed under the left anterior descending coronary artery (LAD) at a location just under the tip of the left atrial appendage. The suture was left to be tied upon occlusion. Lead II ECG and cardiotachometer output were recorded on a Beckman R612.

The rat was allowed to stabilize for several minutes before the administration of drug via the cannulated jugular vein. Compounds were suspended in carbowax, with the total dose (1 mg/kg. unless otherwise indicated) volumes kept below 0.20–0.25 ml. Fifteen minutes after dosing, the LAD was occluded by tying the suture. This procedure provokes severe ventricular arrhythmias, terminating in ventricular fibrillation and death in approximately 73 percent of animals given vehicle only. Data were analyzed based on statistical analysis of heart rate fluctuations. Output from a Beckman cardiotachometer was digitized at 200 msec/pt using a Nicolet 3091 digital oscilloscope, and the data analyzed to yield mean ±variance of the rate for each 1 minute period (300 points). The measured variance for the period 5–11 minutes postocclusion was well correlated with the severity of the observed ventricular arrhythmias, and provided a quantitative measure for the relative antiarrhythmic effectiveness of the compound being tested.

For the purpose of these coronary ligation (C.L.) experiments, the percent ventricular fibrillation, expressed as a percentage of the animals employed, was obtained for purpose of comparison with the control rate of 73 percent in vehicle-treated animals.

Thus, these data establish the compounds of this invention as useful antiarrhythmic agents. The mechanism by which these compounds produce their antiarrhythmic result is not known. The compounds of this invention have demonstrated no meaningful $Ca^{+2}$ antagonist activity, anti-hypertensive activity, or calmodulin inhibition when tested by standard procedures.

Based upon the activity profile elicited by the compounds of this invention in the above-described standard scientifically recognized test model, the compounds are established as anti-arrhythmic agents useful in the treatment of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention. After each example, the percentage incidence of ventricular fibrillation (VF) is presented for comparison with the control incidence of ventricular fibrillation of 73 percent of animals receiving vehicle alone.

EXAMPLE 1

N(1-Methylethyl)-N-[3-(1-Methylethylamino)Propyl]-3(Trifluoromethyl)Benzenesulfonamide m-Trifluoromethylbenzenesulfonylchloride (12.4 g., 0.05 mol) in methylene chloride (50 mL) was added dropwise to N,N'-di-isopropyl propane-1,3-diamine (23.4 g., 0.15 mol) in methylene chloride (400 mL) and the reaction was stirred at room temperature for two hours. The solvent was evaporated and the residue portioned between diethyl ether and 10 percent aqueous sodium hydroxide. After removal of the ether, the residue was chromatographed on DC-alumina (1000) with 3% MeOH/EtOAc to provide the product (12.66 g.). Dissolution in diethyl ether and treatment with isopropanol/HCl gave the hydrochloride salt, (13.24 g.) m.p. 150°-152° C.

Analysis for: $C_{16}H_{25}N_2O_2F_3S.HCl$, Calculated: C, 47.70; 1 H, 6.51; N, 6.95, Found: C, 47.75; H, 6.46; N, 6.55.

VF=0%.

EXAMPLE 2

N-[3-[(1-Methylethyl)Amino]Propyl]-3-(Trifluoromethyl)Benzenesulfonamide

The title compound and its hydrochloride salt were prepared following the procedure of Example 1 with the exception that N-isopropyl-propane-1,3-diamine was employed as the reactant.

Analysis for: $C_{13}H_{10}N_2F_3S.HCl$, Calculated: C, 43.28; H, 5.59; N, 7.76, Found: C, 43.34; H, 5.42; N, 7.84.

VF=0%.

EXAMPLE 3

3,4-Dimethoxy-N-(1-Methylethyl)-N-[3(1-Methylethylamino)-Propyl]-Benzenesulfonamide 3,4 Dimethoxybenzenesulfonyl chloride was reacted with N,N'-diisopropylpropane-1,3-diamine by procedures following those given in Example 1 and chromatographed on Dry-column alumina with 10% methanol/ethyl acetate to provide the title compound. Treatment of this material with isopropanol/HCl gave the hydrochloride salt, m.p. 132°-135° C.

Analysis for: $C_{17}H_{30}N_2O_4S.HCl$, Calculated: C, 51.70; H, 7.91; N, 7.09, Found: C, 51.82; H, 8.11; N, 6.85.

VF=60%; 40% at 10 mg/kg.

EXAMPLE 4

3,4-Dichloro-N-(1Methylethyl)-N-[3-(1-Methylethylamino)Propyl]-Benzenesulfonamide The title compound and its hydrochloride salt were prepared following the procedure of Example 1 with the exception that 3,4-dichlorobenzenesulfonylchloride was used as the reactant. The hydrochloride salt had m.p. 162°-164° C.

Analysis for: $C_{15}H_{24}N_2O_2SCl_2.HCl$, Calculated: C, 44.62; H, 6.24; N, 6.94, Found: C, 44.31; H, 6.01; N, 6.65.

VF=40%.

EXAMPLE 5

N-[4-[(1-Methylethyl)Amino]Butyl]3-Trifluoromethyl)Benzenesulfonamide

4-Aminobutyl-3-trifluoromethyl benzene sulfonamide (0.034 m, 10.30 gms), acetone (6.23 g) and platinum oxide (0.31 gm) in absolute ethanol were reduced with hydrogen at 50 psi for 4 hours. The catalyst was filtered, the solvent removed and the residue crystalized from hexane to provide the title compound, 10.05 g., m.p. 61°-63° C. A portion was treated with HCl in isopropanol to provide the hydrochloride salt of the title compound, m.p. 130°-133° C.

Analysis for: $C_{14}H_{21}N_2O_2F_3S.HCl$, Calculated: C, 44.86; H, 5.92; N, 7.47, Found: C, 45.10; H, 6.05; N, 7.24.

VF=20%.

EXAMPLE 6

N-(1-Methylethyl)-N[4-[(1-Methylethyl)Amino]Butyl]-3(Trifluoromethyl)Benzenesulfonamide 3-Trifluoromethyl benzene sulfonyl chloride (0.104 m, 25.35 g) in methylene chloride (100 ml) was added dropwise to a solution of N,N'-diisopropylbutane,1,4-diamine (0.104 m, 17.86 gm) and diisopropyl ethyl amine (0.104 m, 13.40 g) in methylene chloride (500 ml). The reaction was stirred overnight. The reaction was washed with water, aqueous sodium bicarbonate and then brine and then stripped. The residue was dissolved in diethyl ether, filtered through Supercel to yield the title compound. Treatment with isopropanol/HCl provided the hydrochloric acid salt of the title compound, 14.64 gms, m.p. 175°-176.5° C.

Analysis for: $C_{17}H_{27}N_2O_2F_3S.HCl$, Calculated: C, 48.97; H, 6.77; N, 6.72, Found: C, 48.86; H, 6.63; N, 6.60.

VF=20%.

EXAMPLE 7

N-[2-[bis(1-methylethyl)amino]ethyl]-3,4-dimethoxy-N-(1-methylethyl)-benzenesulfonamide 3,4-Dimethoxybenzene sulfonyl chloride, prepared from veratrole and chlorosulfonic acid was reacted with N,N,N'-triisopropyl ethylene diamine following the procedure of Example 1. The reaction was worked up and the crude product chromatographed on alumina with ethyl acetate. The pure product was obtained, m.r. 69°-71° C.

Analysis for: $C_{19}H_{34}N_2O_4S$, Calculated: C, 59.04; H, 8.87; N, 7.25, Found: C, 58.72; H, 8.90; N, 7.66.

VF=80%.

EXAMPLE 8

N-[2-[(1-methylethyl)amino]ethyl]-3,4-dimethoxy-N-(1-methylethyl)-benzenesulfonamide Reaction of 3,4-dimethoxybenzene sulfonyl chloride with N,N'-diisopropylethylene diamine following the procedure of Example 1 gave a crude crystalline product which on recrystallization from diethyl ether provided the pure title compound, m.r. 53°–55° C.

Analysis for: $C_{16}H_{28}N_2O_4S$, Calculated: C, 55.79; H, 8.19; N, 8.13, Found: C, 55.39; H, 8.13; N, 8.25.

VF=20% at 10 mg/kg.

EXAMPLE 9

3,4-dichloro-N-(1-methylethyl)-N-[2-[(1-methylethyl)-amino]ethyl]benzenesulfonamide 3,4-Dichlorobenzene sulfonyl chloride reacted with an equivalent amount of N,N'-diisopropyl ethylene diamine and tri-ethylamine in methylene chloride following the procedure of Example 1 gave the desired product isolated as a maleate salt, m.r. 200°–202° C.

Analysis for: $C_{14}H_{22}N_2O_2Cl_2S \cdot C_4H_4O_4$, Calculated: C, 46.06; H, 5.58; N, 5.97, Found: C, 45.77; H, 5.49; N, 5.67.

VF=20% at 10 mg/kg.

EXAMPLE 10

4-Hydroxy-N-(1-methylethyl)-N-[2-[(1-methylethyl-amino]ethyl]benzenesulfonamide p-Hydroxybenzene sulfonic acid, sodium salt was converted to the sulfonyl chloride using $SOCl_2/DMF$ and the latter reacted with N,N'-diisopropyl ethylene diamine following the procedure of Example 1 to give the product as a partial methylene chloride solvate, m.r. 153°–155° C.

Analysis for: $C_{14}H_{24}N_2O_3S \cdot 0.15\ CH_2Cl_2$, Calculated: C, 54.27; H, 7.82; N, 8.94, Found: C, 54.48; H, 7.79; N, 8.74.

VF=40% at 10 mg/kg.

EXAMPLE 11

4-Methoxy-N-(1-methylethyl)-N-[2-[(1-methylethyl)-amino]ethyl]benzenesulfonamide Reaction of 4-methoxybenzene sulfonyl chloride with N,N'-diisopropyl ethylene diamine following the procedure of Example 1 gave the product as a gum after removal of some diethyl ether insoluble bis by-product. The monohydrochloride salt was obtained by treatment of the free base with isopropanol/HCl, m.r. 188°–191° C.

Analysis for: $C_{15}H_{27}N_2O_3SCl$, Calculated: C, 51.34; H, 7.76; N, 7.98, Found: C, 51.25; H, 7.85; N, 7.92.

VF=40% at 10 mg/kg.

What is claimed is:

1. A compound of the formula:

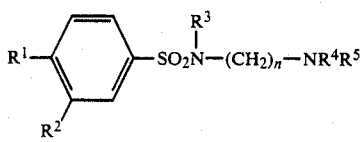

in which

R$^1$ is hydrogen, hydroxyl, alkoxy of 1 to 6 carbon atoms or halo;

R$^2$ is hydrogen, halo or trifluoromethyl, with the proviso that R$^2$ is not hydrogen when R$^1$ is hydrogen;

R$^3$ is isopropyl, or when R$^2$ is trifluoromethyl and R$^1$ is hydrogen, R$^3$ may be hydrogen;

R$^4$ is isopropyl;

R$^5$ is hydrogen or isopropyl; and n is one of the integers 2, 3 or 4;

or a pharmaceutically acceptable salt thereof.

2. The compound of claim 1 which is N-(1-methylethyl)-N-[3-(1-methylethylamino)propyl]-3-(trifluoromethyl)benzenesulfonamide or a pharmaceutically acceptable salt thereof.

3. The compound of claim 1 which is N-[3-[(1-methylethyl)amino]-propyl]-3-(trifluoromethyl)benzenesulfonamide or a pharmaceutically acceptable salt thereof.

4. The compound of claim 1 which is 3,4-dichloro-N-(1-methylethyl)-N-[3-(1-methylethylamino)propyl]-benzenesulfonamide or a pharmaceutically acceptable salt thereof.

5. The compound of claim 1 which is N-[4-[(1-methylethyl)amino]butyl]-3-trifluoromethyl-benzenesulfonamide or a pharmaceutically acceptable salt thereof.

6. The compound of claim 1 which is N-(1-methylethyl)-N-[4-[(1-methylethyl)amino]butyl]-3-(trifluoromethyl)benzenesulfonamide or a pharmaceutically acceptable salt thereof.

7. The compound of claim 1 which is 3,4-dichloro-N-(1-methylethyl)-N-[2-[(1-methylethyl)amino]ethyl]benzenesulfonamide or a pharmaceutically acceptable salt thereof.

8. The compound of claim 1 which is 4-hydroxy-N-(1-methylethyl)-N-[2-[(1-methylethyl)amino]ethyl]benzenesulfonamide or a pharmaceutically acceptable salt thereof.

9. The compound of claim 1 which is 4-methoxy-N-(1-methylethyl)-N-[2-[(1-methylethyl)amino]ethyl]benzenesulfonamide or a pharmaceutically acceptable salt thereof.

10. An anti-arrhythmic composition comprising an anti-fibrillating amount of a compound of the formula:

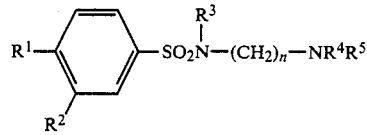

in which

R$^1$ is hydrogen, hydroxyl, alkoxy of 1 to 6 carbon atoms or halo;

R$^2$ is hydrogen, halo or trifluoromethyl, with the proviso that R$^2$ is not hydrogen when R$^1$ is hydrogen;

R$^3$ is isopropyl, or when R$^2$ is trifluoromethyl and R$^1$ is hydrogen, R$^3$ may be hydrogen;

R$^4$ is isopropyl;

R$^5$ is hydrogen or isopropyl; and n is one of the integers 2, 3 or 4;

or a pharmaceutically acceptable salt thereof.

11. A pharmaceutical composition of claim 10 in which said compound is N-(1-methylethyl)-N-[3-(1-methylethylamino)propyl]-3-(trifluoromethyl)benzenesulfonamide.

12. A pharmaceutical composition of claim 10 in which said compound is N-[3-[(1-methylethyl)amino]-propyl]-3-(trifluoromethyl)benzenesulfonamide.

13. A pharmaceutical composition of claim 10 in which said compound is N-[4-[(1-methylethyl)amino]-butyl]-3-trifluoromethyl)-benzenesulfonamide.

14. A pharmaceutical composition of claim 10 in which said compound is N-(1-methylethyl)-N-[4-[(1-methylethyl)amino]butyl]-3-(trifluoromethyl)benzenesulfonamide.

* * * * *